United States Patent [19]

Tremblay et al.

[11] Patent Number: 5,783,210
[45] Date of Patent: Jul. 21, 1998

[54] PHOSPHOLIPID COMPOSITION

[75] Inventors: Paul A. Tremblay, Hamilton; Robert L. Suddith, Robbinsville; John J. Kearns, Princeton, all of N.J.

[73] Assignee: The Liposome Company, Inc., Princeton, N.J.

[21] Appl. No.: 453,132

[22] Filed: May 24, 1995

Related U.S. Application Data

[62] Division of Ser. No. 303,592, Sep. 9, 1994, Pat. No. 5,429,823, which is a continuation of Ser. No. 212,323, Mar. 14, 1994, abandoned, which is a continuation of Ser. No. 512,557, Apr. 12, 1990, abandoned, which is a continuation of Ser. No. 119,572, Nov. 17, 1987, abandoned, which is a continuation-in-part of Ser. No. 938,563, Dec. 5, 1986, abandoned, which is a continuation-in-part of Ser. No. 935,919, Nov. 28, 1986, abandoned.

[51] Int. Cl.$^6$ ................................ A61K 9/127
[52] U.S. Cl. ............................ 424/450; 424/451
[58] Field of Search ................ 210/635, 198.2; 424/450, 551

[56] References Cited

U.S. PATENT DOCUMENTS

| | | | |
|---|---|---|---|
| 2,390,528 | 12/1945 | Freemen et al. | 260/403 |
| 2,727,046 | 12/1955 | Scholfield et al. | 260/403 |
| 2,801,255 | 7/1957 | Scolfield et al. | 260/403 |
| 3,047,597 | 7/1962 | Pardun et al. | 260/403 |
| 3,869,548 | 3/1975 | Wolff | 260/403 |
| 4,157,404 | 6/1979 | Yano et al. | 426/429 |
| 4,224,179 | 9/1980 | Schneider | 264/4.6 |
| 4,235,793 | 11/1980 | Betzing | 260/403 |
| 4,308,166 | 12/1981 | Marchetti et al. | 264/4.6 |
| 4,452,743 | 6/1984 | Günther | 260/403 |
| 4,508,703 | 4/1985 | Redziniak et al. | 436/829 |
| 4,681,582 | 7/1987 | Yamamoto | 604/84 |
| 4,705,806 | 11/1987 | Morton, Jr. | 514/530 |
| 4,714,571 | 12/1987 | Tremblay et al. | 260/403 |
| 4,814,111 | 3/1989 | Kearns | 260/412.4 |

FOREIGN PATENT DOCUMENTS

| | | |
|---|---|---|
| 0 185 235 | 6/1986 | European Pat. Off. |
| 54-61200 | 5/1979 | Japan |

OTHER PUBLICATIONS

Aitzemüller, K., "HPLC and Phospholipids Part I: General Considerations", Fette. Seifen Anstrichmittel, 86:318–322 (1984).
Alam, et al., "Novel system for separation of phospholipids by High performance liquid chromatography", J of Chrom, 234:218–221.
Bahrami, et al., "A P{reparative High Performance Liquid Chromatography Method for Separation of Lecithin: comparison to Thin–Layer Chromatography", Journal of Lipid Research, 28:596–8 (1987).
Blank, et al., "Improved High Performance Liquid Chromatographic Method for Isolation of Platelet–Activating Factor from Other Phospholipids", Journal of Chromatography, 273:415–420 (1983).
Chen, et al., "Measurement of Etanolamine–and Serine–Containing Phospholipids by High–Performance Liquid Chromatography with Fluorescence Detection of Their Dns Derivatives", Journal of Chromatography, 208:339–346 (1981).
Chen, et al., "Improved Procedure for the Separation of Phospholipids by High–Performance Liquid Chromatography", Journal of Chromatography, 227:25–31 (1982).
Fager, et al., "A Large-Scale Purification of Phosphatidylethanolamine, Lysophosphatidylethanolamine, and Phosphatidylcholine by high performance liquid chromatography: a Partial Resolution of Molecular Species", Journal of Lipid Research 18: 704–709 (1977).
Geurts van Kessel, et al., "High Performance Liquid Chromatographic Separation and Direct Ultraviolet Detection of Phospholipids", BBA 486:524–530 (1977).
Gross, et al., "Isocratic High–Performance Liquid Chromatography Separation of Phosphoglycerides and Lysophosphoglycerides", Journal of Chromatography, 197:79–85 (1980).
Hamilton, et al., "Unilamellar liposomes made with French pressure cell: a simple preparative and semiquanititative technique", 1980, J. of Lipid Research, vol. 21, 981–992.
Hanson, et al., "High–Performance Liquid Chomatographic Analysis of Egg Yolk Phospholipids", J. Chroma, 205:393–400 (1981).
Hax, et al., "High–Performance Liquid Chromatographic Separation and Photometric Detection of Phospholipids", J. Chroma, 142:735–741 (1977).
Jungalwala, et al., "High–Performance Liquid Chromatography of Phosphatidylcholine and Sphingomyelin with Detection in the Region of 200 nm", Biochem. J. 155:55–60, (1976).
Lea, et al., "Phospholipids", Biochem. J., 60:353–363 (1955).
Lundberg, "Properties of Mixed Vesicles of Lecithin: Cholesterol up to a 1:2 Mol Ratio", Chemistry and Physics of Lipids, 18(1977) 212–220.
MacDonald, et al., "Dry Column Chromatography of Phospholipids", J Chroma, 131:157–168 (1977).
Nasner, et al., "Trunnung einiger Bestandteile des Lecithins mit Hilfe der Hochleistunge–Flüssigkeits–Chromatographie, II. J. Chroma, 216:389–394 (1981).

(List continued on next page.)

*Primary Examiner*—Thurman K. Page
*Assistant Examiner*—D. Faulkner
*Attorney, Agent, or Firm*—Kenneth B. Rubin

[57] ABSTRACT

A composition having equal to or greater than about 97 percent by weight phosphatidylcholine and about equal to or less than about 3 percent by weight to about 0.5% sphingomylin and equal to or less than about 0.5% lysophosphatidylcholine (undetectable by UV at 205 nm) has been found to result in liposomes having improved stability. Methods for preparing the composition are disclosed whereby the phospholipids are extracted and then purified using silica chromatography.

12 Claims, No Drawings

OTHER PUBLICATIONS

Nasnet, et al., "Analysis of Phospholipids in the Lecithin Processing Industry", Doctoral Dissertation, Dept. of Biology, University of Hamburg, (1981).

Nicholas, et al., "Synthesis of Mixed-Acid Phosphatidylcholine and High Pressure Liquid Chromatographic Analysis of Lysophosphatidylcholines", Lipids, 18:434-438 (1983).

Patel, et al., "Rapid, Large-Scale Purification of Crude Egg Phospholipids Using Radially Compressed Silica Gel Columns", J Chroma, 150:542-547 (1978).

Rainey, et al., "Simplex Optimization of the Separation of Phospholipids by High-Pressure Liquid Chromatography and Thin-Layer Chromatography", Analytic Chimica Acta 93:211-219 (1977).

Rivnay, B., "Combined Analysiss of Phospholipids by High-Performance Liquid Chromatography and Thin-Layer Chromatography", J. Chroma, 294:303-315 (1984).

Singleton, et al., "Chromatographically Homogenous Lecithin from Egg Phospholipds", Journal of the American Oil Chemists Society, 42:53-55 (1965).

Smith, et al., Principles of Biochemistry, 7th Ed. 115-121, 273-281, 1983.

Untracht, et al., J. Bio. Chem. vol. 252:4449-4457, 1977.

Yandrasitz, et al., "High-performance Liquid Chromatography of Phospholipids with UV Detection: Optimization of Separations on Silica", J Chroma, 225:319-328 (1981).

Rivnay, B., "Combined Analysiss of Phospholipids by High- Performance Liquid Chromatography and Thin-Layer Chromatography", J. Chroma, 294:303-315 (1984).

PHOSPHOLIPID COMPOSITION

RELATED PENDING APPLICATIONS

This application is a division of U.S. Ser. No. 08/303,592, filed Sep. 9, 1994, now U.S. Pat. No. 5,429,823 which is a continuation of U.S. Ser. No. 08/212,323, filed Mar. 14, 1994, now abandoned, which in turn is a continuation of U.S. Ser. No. 07/512,557, filed Apr. 12, 1990, now abandoned, which in turn is a continuation of U.S. Ser. No. 07/119,572, filed Nov. 17, 1987, now abandoned, which in turn is a continuation-in-part of U.S. Ser. No. 938,563, filed Dec. 5, 1986, now abandoned, which in turn is a continuation-in-part of U.S. Ser. No. 06/935,919, filed Nov. 28, 1986 and now abandoned.

FIELD OF THE INVENTION

This invention is directed to a mixture of phospholipids. More particularly, this invention relates t o a discrete range of mixtures of phosphatidylcholine and sphingomyelin, substantially absent lysophosphatidyl choline, which are of pharmaceutical production quality directly useful for preparing stable liposomes.

BACKGROUND OF THE INVENTION

Liposomes are completely closed lipid bilayer membranes containing an entrapped aqueous volume. Liposomes may be unilamellar vesicles (possessing a single membrane bilayer) or multilamellar vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (non-polar) "tails" of the lipid monolayers orient toward the center of the bilayer while the hydrophilic (polar) "heads" orient toward the aqueous phase. Liposomes are useful for delivering bioactive agents such as drugs to mammals, including humans.

Generally, a principal ingredient of the lipid bilayers are phospholipids such as phosphatidyicholine. The resulting liposomes are often unstable and degrade over time. This instability may make the pharmaceutical use and commercial development of liposomal drug delivery systems less attractive because of the reduced shelf-life of the products or the need to take special care in storing the products.

The analysis of lipid composition may be performed by a variety of methods. Among those methods are high performance liquid chromatography using ultraviolet detection at 205 nm ("UV at 205 nm"); thin layer chromatography of phospholipids using a phosphorus specific assay based on the zinzadze reagent (such as Phospray™, Supelco Co.) ("TLC"); high pressure liquid chromatography using flame ionization; and thin layer chromatography using flame ionization (e.g., Iatroscan (TH-10)™, Iatron Laboratories, Inc., Japan). Each method will yield results peculiar to the test method. The lipid compositions of this invention have been analysed by both UV at 205 nm and TLC. The UV at 205 nm test method utilized herein is accomplished by high performance liquid chromatography on a silica gel column. The TLC test method as utilized herein is accomplished by spotting about a 200 ug sample of egg phosphatidylcholine ("EPC") on a silica gel plate (such as HPTLC-HL preadsorbant plate, Analtech, Inc.). UV at 205 nm as compared to TLC tests of identical materials produced slightly higher apparent purity for the UV at 205 nm tests.

Purities noted herein will be expressed based upon TLC analysis unless otherwise stated.

SUMMARY OF THE INVENTION

We have found lipid compositions which result in the formation of more stable liposomes.

Also disclosed is a method for preparing the lipid composition of the present invention comprising the step of isolating the lipid composition with a liquid chromatographic column by eluting with a hexane-ethanol-water gradient. Further disclosed are liposomes prepared with the novel lipid composition and said liposomes further comprising at least one bioactive agent.

DETAILED DESCRIPTION OF THE INVENTION

A convenient process for obtaining the desired composition is to begin with egg yolks. With egg yolks the preferred starting material is frozen egg yolks although other sources of egg yolks, such as fresh, spray-dried, freeze-dried, evaporation or desiccant dried egg yolks may also be employed. In another embodiment the starting material is a partially purified phosphatidylcholine preparation (80% phosphatidylcholine) which is commercially available.

In one embodiment the starting material is frozen egg yolks, partially thawed. To partially thaw the frozen egg yolks they are maintained at about 4° C. for about 16–34 hours so that about 20–50 percent of the egg yolk has thawed. The partially thawed egg yolk solids are extracted twice with ethanol. These extractions result primarily in the dehydration of the egg yolk solids with some minor extraction of phospholipid and neutral lipid oil from the egg yolk solids. The dehydration operation is preferred to prevent formation of a two-phase mixture when hexane is used for further extraction of the phospholipids and renders later filtration easier. If spray drying, vacuum drying, lyophilization, or other means are used to dry the egg yolks, these ethanol extraction process steps may be reduced or eliminated. Generally the ratio on a volume-to-weight basis of ethanol to egg yolk solid is between about 20:1 and 1:1 for each extraction, preferably between about 2:1 and 1:1. The temperature at which the extraction is carried out is generally between about 60° and 0° C., preferably between about 40° and 30° C.

The dehydrated egg yolk solids obtained following ethanol extraction are extracted one or more times and preferably three times with a mixture of ethanol and hexane. Each extraction consists of (a) mixing the egg yolk solids and the ethanol-hexane mixture followed by (b) filtration to collect the egg yolk solids. Hexane is then removed from the extract. Conveniently, the extract (filtrate) from each extraction is subjected to vacuum distillation to evaporate off the hexane. The ratio of ethanol to hexane in the ethanol-hexane extracting mixture is between about 99.9:1 and 1:99.9 by volume, preferably between about 1:2 and 2:1. The weight-to-volume ratio of the egg yolk solids to the ethanol-hexane mixture is between about 1:200 and 1:0.5, preferably between about 4:1 and 1:1, more preferably about 2:1. The temperature at which this step is carried out is between about 60° C. and −20° C., preferably between about 40° C. and 20° C., more preferably between about 40° C. and 35° C. The filtration is carried out by vacuum filtration. Other methods for the separation of the solids and liquids known in the art such as pressure filtration, centrifugation, filter press, sieving and the like may also be employed.

In order to prevent the formation of hydroperoxides, peroxides and degradation and coloring of the phosphatidylcholine ("PC") during preparation of the compositions of the present invention, precautions can be taken to prevent oxidation during processing. For example, an antioxidant such as butylated hydroxyltoluene ("BHT") or alpha-tocopherol can be added during the ethanol-hexane extraction of the egg yolk solids. Thus, BHT at a concentration of about 2 mg per liter of solvent can be employed. Alternatively, other procedures to exclude oxygen such as the use of an inert atmosphere such as nitrogen can be employed.

The initial ethanol extracts and the substantially "hexane-free" ethanol-hexane extracts are then pooled. The ethanol extracts also contain some water which renders the neutral lipids insoluble while the phospholipids remain soluble. On sitting at about 20°–30° C., generally for about 4–18 hrs., a dense "oil" layer forms under the aqueous ethanol layer. The phospholipids remain in the ethanol fraction are used as the feed material for the next process step. The oil layer is separated and discarded. The oil layer contains primarily neutral lipids and cholesterol thus providing substantial purification of the ethanolic extract.

The ethanol fraction is then extracted at least one and preferably three times with hexane after addition of water to the ethanol fraction. The volume-to-volume ratio of water to ethanol is between about 10:1 and 1:10, preferably between about 1:2 and 1:3. The volume-to-volume ratio of ethanol to hexane is between about 1:10 and 10:1, preferably between about 4:1 and 1:1. Each extraction step consists of (a) addition of hexane to the ethanol-water fraction followed by (b) addition of an aliquot of water; (c) mixing of the solution; (d) phase separation (generally up to about 2 days are required). This separation can be accelerated by centrifugation or other methods known to enhance phase separation.) and (e) collection of the hexane phase. The three hexane phases are combined and the hexane is removed preferably by vacuum distillation, to yield about a 20% (w/v) phospholipid solution in hexane. The temperature at which this extraction step occurs is between about −20° and 60° C., preferably between about 15° and 35° C., more preferably between about 15°–25° C.

Because of its toxicity and adverse effect on liposome stability, lysophosphatidylcholine is an unwanted component of phosphatidylcholine compositions. The composition of the present invention has equal to or less than about 0.5% (0.2% UV at 205 nm—the limit of detection) by weight of lysophosphatidylcholine (the limit of detection) and the method disclosed herein results in the separation of the lysophosphatidylcholine fraction as it remains mostly in the ethanol water phase. "Substantially absent lysophosphatidylcholine" as used herein shall mean less than about 0.5% lysophosphatidylcholine by weight.

The 20% (w/v) phospholipid solution is the starting material for the liquid chromatographic, preferably HPLC, separation of lipid composition of the present invention from the phospholipid mixture. This material is preferably loaded on silica gel chromatographic medium having a particle size between about 5 and 500 microns, preferably between about 20–40 micron particle silica column. For this invention, generally any silica suitable for chromatography can be employed; for example, porous silica or fused silica, spherical silica or irregular shaped silica with small or large pores. The mobile phase is a step gradient of hexane-ethanol-water. Generally about 20 liters of the mobile phase are required for 0.7 liters of the phospholipid solution using a 5 cm diameter, 50 cm long column. The volume ratio of the first solvent hexane-ethanol-water is chosen so that a single phase is present and can, for example, vary from about 10:90:1 to 100:100:3, preferably about 60:130:1 to 60:130:8; and more preferably about 60:130:6. The neutral lipid, cholesterol and phosphatidylethanolamine are eluted in this solvent. Following elution of the cholesterol and phosphatidylethanolamine, the mobile phase is changed to a solvent containing more water. The volume ratio of the second solvent hexane-ethanol-water is chosen so that a single phase is present and can, for example, vary from about 100:100:4 to about 20:100:10, preferably about 60:130:1 to about 60:130:14, and more preferably about 60:130:12. Phosphatidylcholine and sphingomyelin elutes in this solvent. Approximately 160 gms of the desired lipid composition product can be obtained from extraction of 4 kg of egg yolks. The composition of the product can be determined by thin layer chromatography and analytical HPLC.

During the elution with the second eluant hexane-ethanol-water, "tailing" can occur which prevents the clean separation of the desired phosphatidylcholine-sphingomyelin product. In order to reduce tailing, trifluoroacetic acid (TFA) acetic acid or other organic acids, or simple ammonium salts such as ammonium sulfate or ammonium chloride can be added to the eluting solvent. The concentration of TFA can be between about $10^{-6}$ and $10^{+1}$ milliliters per liter of eluting solvent, preferably about $10^{-3}$ ml per liter. For the ammonium salt the concentration can be between about $10^{-6}$ and $10^{+1}$ milligram per liter of eluting solvent, preferably about $10^{-3}$ mg per liter.

The lipid composition product is collected from the HPLC eluting solvent by addition of water and evaporation of the hexane layer. The lipid composition can, for example, be redissolved in ethanol or ethanol-hexane solution such as 5% by volume ethanol in hexane to a final concentration of 10% (w/v) and stored at 4° C. in amber bottles. Of course, any solvent generally used for solubilization of lipid can be employed for solubilization of the lipid composition product.

The extraction and chromatographic procedures of the present invention can also be applied to soya and other sources of phosphatidylcholine. Commercially available lecithin granules (such as those available from American Lecithin or Central Soya) generally having about 25 percent by weight of phosphatidylcholine are a convenient starting materials. The lecithin granules are extracted at least one, preferably about five times with ethanol. Each extraction consists of addition of 4 volumes (by weight) of ethanol to the lecithin granules, mixing, and collection of the extract by filtration. The ethanol fractions are pooled and filtered. The pooled ethanol fractions are extracted with water and hexane as above. Approximately 200 gms of phospholipid are obtained when 1 kg of lecithin granules are extracted.

The five hexane extracts are concentrated, preferably by vacuum distillation, to yield a 20% (w/v) solution of phospholipid.

The 20% (w/v) phospholipid in hexane solution is leaded directly onto the HPLC silica column for separation of phosphatidyl choline. Approximately 160 gm of phosphatidyl choline (80% recovery) is obtained. The phosphatidylcholine fraction is approximately 98% pure with the remainder being sphingomyelin the product being substantially free of lysophosphatidylcholine. The phosphatidylcholine-sphingomyelin fraction is concentrated by vacuum distillation. The resulting phosphatidylcholine-sphingomyelin can be stored as a 20% (w/v) solution in ethanol.

Another process utilizes, as a starting material, a phospholipid preparation which is about 80% phosphatidylcholine and is commercially available (e.g., Lipoid KG, Ludwigshafen, West Ger.) The 80% phosphatidylcholine is employed in the purification in the 20% (w/v) phospholipid in hexane which is loaded directly onto the HPLC silica column. Thus in this process the 20% (w/v) of 80% phosphatidylcholine is what is applied to the HPLC column. In a preferred process a 4 inch diameter HPLC column is utilized.

It is a critical limitation of the instant invention that the final product is of a lipid composition determined to be ideal for high stability and low toxicity. This composition is at least about 97% phosphatidylcholine and at least about 0.5% sphingomyelin to about 3% sphingomyelin by weight and further that the composition be substantially absent lysophosphatidylcholine. More preferably the composition is at least about 1.5% sphingomyelin and more preferably at least about 2% sphingomyelin.

The production of a material that is in the exact mixture for use in the final product is a particularly efficient method of purification. Previously, to obtain a specific composition of a desired end product ("pharmaceutical production quality") pure phosphatidylcholine would be mixed with other constituents to yield the desired formulation. All constiuents would necessarily be "over purified" and then combined. This expended reagents, time and energy and further unnecessarily raised costs. By the instant method the desired pharmaceutical production quality material is the output of the process.

As to liposome preparations, the original liposome preparation of Bangham et al. (*J. Mol. Biol.*, 13: 238–252 (1965)) involves suspending phospholipids in an organic solvent which is then evaporated to dryness leaving a phospholipid film on the reaction vessel. Then an appropriate amount of aqueous phase is added, the mixture is allowed to "swell", and the resulting liposomes which consist of multilamellar vesicles (MLVs) are dispersed by mechanical means. This technique provides the basis for the development of the small sonicated unilamellar vesicles described by Papahadjopoulos et al. (*Biochim. Biophys. Acta.* 135, 624–638 1967), and large unilamellar vesicles.

Large unilamellar vesicles may be produced using an extrusion apparatus by a method described in Cullis et al., U.S. patent application Ser. No. 788,017, filed Oct. 16, 1985 entitled "Extrusion Technique for Producing Unilamellar Vesicles", relevant portions of which are incorporated herein by reference. Vesicles made by this technique, LUVETS, are extruded under pressures of up to about 700 psi through a polycarbonate membrane filter. These vesicles may be exposed to at least one freeze and thaw cycle prior to the extrusion technique; this procedure is described in Bally et al., U.S. Ser. No. 06/800,545, filed Nov. 21, 1985, now abandoned, relevant portions of which are incorporated herein by reference.

Other techniques that are used to prepare vesicles include those that form reverse-phase evaporation vesicles (REV), Papahadjopoulos et al., U.S. Pat. No. 4,235,871, stable plurilamellar vesicles (SPLV), Lenk et al., U.S. Pat. No. 4,522,803 and incorporated herein by reference, monophasic vesicles, (MPV) Fountain et al., U.S. Pat. No. 4,588,578 and incorporated herein by reference, and freeze and thaw multilamellar vesicles (FATMLV), Bally et al. U.S. patent application Ser. No. 752,423 filed Jul. 5, 1985, Ser. No. 06/800,545 filed Nov. 21, 1985, and now abandoned, both of which are incorporated herein by reference, and vesicles that have equal distribution of solute, Lenk et al., U.S. patent application Ser. No. 660,573, filed Oct. 12, 1984, now U.S. Pat. No. 5,030,053 incorporated herein by reference.

A variety of sterols and their water soluble derivatives have been used to form liposomes; see specifically Janoff et al., U.S. application Ser. No. 773,429, filed Sep. 10, 1985 entitled "Steroidal Liposomes", Mayhew et al., WO 85/00968, published Mar. 14, 1985, describe a method for reducing the toxicity of drugs by encapsulating them in liposomes comprising alpha-tocopherol and certain derivatives thereof. Also, a variety of tocopherols and their water soluble derivatives have been used to form liposomes, see Janoff et al., Ser. No. 786,740, filed Oct. 15, 1986 entitled "Alpha-Tocopherol-Based Vesicles" and incorporated herein by reference.

The method for preparing the sterol vesicles involves adding to an aqueous buffer a salt form of an organic acid derivative of a sterol capable of forming closed bilayers in an amount sufficient to form completely closed bilayers which entrap an aqueous compartment. A suspension of multilamellar vesicles is formed by shaking the mixture. The formation of vesicles is facilitated if the aqueous buffer also contains the counterion of the salt in solution.

The application of energy to the suspension, e.g., sonication, or extrusion of the vesicles through a French pressure cell (French Press) or through a porous filter of the appropriate pore size, will convert the multilamellar sterol vesicles to unilamellar vesicles.

The liposomes prepared using the lipids of the present invention can be multilamellar or unilamellar. Multilamellar liposomes may be made by any method known in the art and include SPLVs, freeze and thaw MLVs, REVs and MPVs. Unilamellar liposomes may be formed by a freeze and thaw technique followed by an extrusion through polycarbonate filters.

Liposomes entrap an aqueous medium which is enclosed by the lipid bilayers. The aqueous medium can be for example, water or water containing a dissolved salt or buffer. Examples of such salts or buffers can be sodium chloride and phosphate buffered saline (PBS). Other buffers include but are not limited to borate, citrate, Tris-HCl (Tris-(hydroxymethyl)-aminomethane hydrochloride), and HEPES (N-2-hydroxyethyl piperazine-$N^1$-2-ethane sulfonic acid). Buffers may be in the pH range of between about 2.0 and about 14.0. In the preferred embodiment, the preparations are hydrated with HEPES buffer (150 mM NaCl, 20 mM HEPES), pH 7.0, borate buffer (100 mM $Na_2HCO_3$, 50 mM $H_3BO_3$, pH 8.5, or citrate buffer (150 MM Na-citrate), pH 8.5.

In a liposome-drug delivery system, the medicament is entrapped in the liposome and then administered to the patient to be treated. For example, see Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179, Lenk. et al., U.S. Pat. No. 4,522,803, and Fountain et al., U.S. Pat. No. 4,588,578.

Virtually any bioactive agent can be entrapped within the liposomes for use according to the present invention. Such agents include but are not limited to antibacterial compounds such as gentamicin, antiviral compounds such as rifampacin, antifungal compounds such as amphotericin B, anti-parasitic compounds such as antimony derivatives, antineoplastic compounds such as vinblastine, vincristine, mitomycin C, doxorubicin, daunomycin, methotrextate, and cisplatin, among others, proteins such as albumin, toxins such as diptheria toxin, enzymes such as catalase, hormones such as estrogens, neurotransmitters such as acetylcholine, lipoproteins such as alpha-lipoprotein, glycoproteins such as hyaluronic acid, immunoglobulins such as IgG, immunodulators such as the interferons or the interleukins, dyes such as Arsenazo III, radiolabels such as $^{14}C$, radio-opaque compounds such as $^{99}Te$, fluorescent compounds such as carboxy fluoroscein, polysaccharides such as glycogen, cell receptor binding molecules such as estrogen receptor protein, non-steroidal anti-inflammatories such as indomethacin, salicylic acid acetate, ibuprofen, sulindac, piroxicam, and naproxen; anti-inflammatories such as dexamethasone, antiglaucomic agents such as timolol or pilocarpine, anesthetics such as dibucaine, nucleic acids such as thymine, polynucleotides such as RNA polymers.

The liposomes may be dehydrated, thereby enabling storage for extended periods of time until use. Standard freeze-drying equipment or equivalent apparatus may be used to dehydrate the liposomes. Liposomes may also be dehydrated simply by placing them under reduced pressure. Alternatively, the liposomes and their surrounding medium can be frozen in liquid nitrogen prior to dehydration. Dehydration with prior freezing may be performed in the presence of one or more protective sugars in the preparation, according to the process of Janoff et al., U.S. application Ser. No. 759,419, filed Jul. 26, 1985, entitled "Dehydrated Liposomes", relevant portions of which are incorporated herein by reference. Examples of protective sugars that may be used include but are not limited to trehalose, maltose, sucrose, glucose, lactose and dextran. Alternatively, multi-lamellar vesicles may be dehydrated with prior freezing without protective sugars. When the dehydrated liposomes are to be used, rehydration is accomplished by simply adding an aqueous solution, e.g., distilled water, to the liposomes and allowing them to rehydrate.

The medicaments are administered within liposomes, in admixture with a pharmaceutically-acceptable carrier selected with regard to the intended route of administration and standard pharmaceutical practice. Dosages for these medicaments when entrapped in liposomes will generally be about that of the drugs alone; dosages will be set by the prescribing physician with regard to the age, weight and condition of the patient. The proportional ratio of active ingredient to carrier will naturally depend on the chemical nature, solubility and stability of the active ingredient, as well as the dosage contemplated. For the oral mode of administration, a liposome composition of this invention can be used in the form of tablets, carriers which can be used include lactose, sodium citrate, and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, certain sweetening and/or flavoring agents can be added. For parenteral administration or injection via intravenous, intraperitoneal, intramuscular, subcutaneous, or intra-mammary route, sterile solutions of the liposome composition are prepared. For intravenous use, the total concentration of solutes should be controlled to render the preparation isotonic.

In another example of their use, vesicle-entrapped compounds may be incorporated into a broad range of topical dosage forms including but not limited to gels, oils, emulsions and the like. For instance, the suspension containing the entrapped compound may be added to the aqueous phase as an ingredient in the liposome preparation. Such preparations may be administered as topical creams, pastes, ointments, gels, lotions and the like for direct application.

EXAMPLE 1

Preparation from Egg Yolk

Partially thawed egg yolks (7.3 kilograms) were extracted two times with 9 L each time of absolute ethanol. The filtrates were pooled (16.7 Litres total volume) and the filter cake was extracted three more times at 38° C. with solutions of hexane-ethanol consisting first of 3 liters of ethanol and 4 liters of hexane, second of 2 liters of ethanol and 4 liters of hexane and finally with 1.5 liters of ethanol and 3.5 liters of hexane. The hexane-ethanol egg extracts were pooled (16.7 liters) and the hexane was evaporated in a rotoevaporator at 40° C. with a vacuum of 100 millimeters of mercury. The residual ethanolic egg extract was pooled with the aqueous ethanol first two pooled extracts (total 18 liters) and the resulting mixture was left to settle for 2 days. The neutral lipids, triglycerides and cholesterol and some orange pigments oiled out of solution and were separated. The supernatant ethanol-water (16.3 liters) was extracted with 2 liters of hexane and 3 liters of water in order to make the ratio about 2.5:1 ethanol:water. The extracted solvent mixture was stirred and allowed to separate until the ethanol water phase is cleared. The hexane phase is removed, kept and the aqueous ethanolic phase was reextracted two more times with 2 liters of hexane and 1 liter of water each. The three hexane extracts were pooled and the hexane evaporated until a 20% weight to volume solution of phospholipid was obtained. The 20% solution consisted of 70% phosphatides and 30% neutral lipid. 4 L of 20% solution (i.e., 800 g of phosphatides) was obtained.

650 mL of 20% hexane solution of phosphatides was loaded onto a silica gel column (5 cm×50 cm) with 490 g of silica, 25–40 micron in size with 60 angstrom pores (YMC-GEL, SIL60, 350/500 mesh, Yamamaura Chemical Laboratory Co., Japan). The neutral lipids and phosphatidyl ethanolamine were eluted with 5 liters of solvent consisting of hexane:ethanol:water 60:130:6 by volume pumped at 60 mL/minute. This is collected as the first fraction. The desired product was eluted with 18 L of solvent B consisting of hexane:ethanol:water 60:130:12 v/v/v pumped at 80 mL/minute. The eluant between A and B solvent is taken in 5×400 mL fractions. The remaining is collected as the desired product. All the fractions were analyzed by TLC and those judged clear of phosphatidylethanolamine, in this case the last 3 of the 400 mL fractions and the large final fraction were pooled and three liters of water was added in order to make the ratio of ethanol to water at 2.5:1. The hexane phase was removed from the ethanol-water phase and saved. The ethanol-water phase was extracted twice more with two liters of hexane and two and three more liters of water, respectively. The combined hexane extracts were pooled and evaporated to a 10% solution. Yield: 65 g of equal to or greater than alout 97% (98% UV at 205 nm) pure phosphatidylcholine with equal to or less than about 3% (1.9% UV at 205 nm) to at least about 0.5% sphingomyelin, equal to or less than about 0.5% (0.2% UV at 205 nm) lysophosphatidylcholine, no phosphatidylethanolamine and no cholesterol or other neutral lipids.

EXAMPLE 2

Preparation from 80% Phosphatidvlcholine

The preparation using commercially available phospholipid of at least 80% phosphatidylcholine (Lipoid KG) used the procedure of Example 1 at the point where three hexane extracts were pooled and the hexane evaporated until a 20% weight to volume solution of phospholipid was obtained. Instead of the 20% solution consisting of 70% phosphatides and 30% neutral lipid the 80% phosphatidylcholine material (in this batch, 81.2%) was substituted.

5,000 mL of 20% solution of the 80% phosphatidylcholine in hexane was loaded onto a silica gel column (4 in.×48 in.) filled with silica, 20 micron in size with 60 angstrom pores (Separations Technology Inc., Wakefield, R.I.). The neutral lipids and phosphatidyl ethanolamine were eluted with 30 liters of solvent consisting of hexane:ethanol:water 60:130:6 by volume pumped at 350 mL/minute. This is collected as the first fraction. The desired product was eluted with 102 L of solvent B consisting of hexane:ethanol:water 60:130:12 by volume pumped at 350 mL/minute. 4 L fractions were then collected for analysis. All the fractions were analyzed by TLC and those judged clear of phosphatidylethanolamine, in this case the last 96 L were clear. 16 L portions were placed in a 22 L separation funnel and 4 L of water was added in order to make the ratio of ethanol to water at 2.5:1(v/v). The hexane phase was removed from the ethanol-water phase and saved. The ethanol-water phase was extracted once more with four liters of hexane. The combined hexine extracts were pooled and evaporated to dryness. Yield: 195 g of equal to or greater than about 97% (98% UV at 205 nm) pure phosphatidylcholine with equal to or less than about 3% (1.9% UV at 205 nm) to at least about 0.5% sphingomyelin, equal to or less than about 0.5% (0.2% UV at 205 nm) lysophosphatidylcholine, no phosphatidylethanolanine and no cholesterol or other neutral lipids.

We claim:

1. A method of preparing a pharmaceutical quality lipid composition from a mixture comprising lipids which comprises:

(a) applying the lipid to a silica gel chromatographic medium comprising particles having sizes of from about 5 microns to about 500 microns;

(b) eluting the medium with a first mobile phase comprising hexane, ethanol and water;

(c) eluting the medium with a second mobile phase comprising:

(i) hexane;
(ii) ethanol;
(iii) water; and,
(iv) an organic acid or an ammonium salt; and, (d) collecting the eluate.

2. The method of claim 1, wherein the particle has a size of from about 20 microns to about 40 microns.

3. The method of claim 1, wherein the chromatographic medium is a high performance liquid chromatographic medium.

4. The method of claim 1, wherein the first mobile phase comprises hexane, ethanol and water in a volume ratio of from about 10:90:1 to about 100:100:3.

5. The method of claim 3, wherein the volume ratio is from about 60:130:1 to about 60:130:8.

6. The method of claim 4, wherein the volume ratio is about 60:130:6.

7. The method of claim 1, wherein the second mobile phase comprises hexane, ethanol and water in a volume ratio of from about 100:100:4 to about 20:100:10.

8. The method of claim 6, wherein the volume ratio is from about 60:130:1 to about 60:130:14.

9. The method of claim 8, wherein the volume ratio is about 60:130:12.

10. The method of claim 1, wherein the second mobile phase comprises the organic acid trifluoroacetic acid.

11. The method of claim 10, wherein the concentration of trifluoroacetic acid in the second mobile phase is between about $10^{-6}$ and 10 milliliters per liter.

12. The method of claim 10, wherein the concentration of trifluoroacetic acid in the second mobile phase is about $10^{-3}$ milliliters per liter.

* * * * *